United States Patent
Rostami et al.

(10) Patent No.: US 10,306,927 B2
(45) Date of Patent: Jun. 4, 2019

(54) VENTURI EFFECT-DRIVEN FORMULATION DELIVERY IN E-VAPING DEVICES

(71) Applicant: Altria Client Services LLC, Richmond, VA (US)

(72) Inventors: Ali Rostami, Richmond, VA (US); Raymond Lau, Richmond, VA (US); Eric A. Hawes, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/222,183

(22) Filed: Jul. 28, 2016

(65) Prior Publication Data

US 2018/0027875 A1    Feb. 1, 2018

(51) Int. Cl.
| | |
|---|---|
| A24F 25/00 | (2006.01) |
| A24F 47/00 | (2006.01) |
| B05B 7/04 | (2006.01) |
| H05B 3/42 | (2006.01) |
| A61M 15/06 | (2006.01) |
| A61M 11/04 | (2006.01) |
| G08B 5/36 | (2006.01) |
| A61M 16/00 | (2006.01) |
| A61M 15/00 | (2006.01) |

(52) U.S. Cl.
CPC ......... *A24F 47/008* (2013.01); *A61M 11/042* (2014.02); *A61M 15/06* (2013.01); *B05B 7/0416* (2013.01); *H05B 3/42* (2013.01); *A61M 15/0003* (2014.02); *A61M 2016/0015* (2013.01); *A61M 2205/3653* (2013.01); *A61M 2205/8206* (2013.01); *G08B 5/36* (2013.01); *H05B 2203/021* (2013.01)

(58) Field of Classification Search
CPC .... A24F 47/002; A24F 47/004; B05B 7/0416; G08B 5/36; H05B 3/42; H05B 2203/021
USPC .................................................. 131/329, 330
See application file for complete search history.

(56) References Cited

U.S. PATENT DOCUMENTS

| | | |
|---|---|---|
| 5,487,378 A | 1/1996 | Robertson et al. |
| 5,894,841 A * | 4/1999 | Voges .................. A24F 47/008 128/200.14 |
| 6,260,549 B1 | 7/2001 | Sosiak |

(Continued)

FOREIGN PATENT DOCUMENTS

| | | |
|---|---|---|
| DE | 202015006397 U1 | 12/2015 |
| WO | WO-2014/177859 A1 | 11/2014 |

(Continued)

OTHER PUBLICATIONS

International Search Report and Written Opinion dated Oct. 13, 2017 for corresponding International Application No. PCT/EP2017/069246.

*Primary Examiner* — Khiem M Nguyen
(74) *Attorney, Agent, or Firm* — Harness, Dickey & Pierce, P.L.C.

(57) ABSTRACT

Example embodiments relate to an e-vaping device including a mouth-end insert, a reservoir connectable to the mouth-end insert, the reservoir including a hollow portion along a longitudinal axis of the e-vaping device, a plurality of orifices distributed along an interior surface of the reservoir, and a power portion connectable to the reservoir. The e-vaping further includes a portion configured to direct an amount of pre-vapor formulation onto the heater.

19 Claims, 7 Drawing Sheets

(56) References Cited

U.S. PATENT DOCUMENTS

| | | |
|---|---|---|
| 6,994,083 B2 | 2/2006 | Foley et al. |
| 7,913,688 B2* | 3/2011 | Cross .................. A61M 11/041 128/203.24 |
| 8,833,364 B2 | 9/2014 | Buchberger |
| 9,162,004 B1 | 10/2015 | Ansley et al. |
| 2010/0242975 A1* | 9/2010 | Hearn .................. A24F 47/002 131/273 |
| 2012/0167878 A1 | 7/2012 | Belson et al. |
| 2013/0061861 A1 | 3/2013 | Hearn |
| 2014/0212334 A1 | 7/2014 | Klein et al. |
| 2014/0334802 A1 | 11/2014 | Dubief |
| 2014/0373831 A1 | 12/2014 | Culbertson et al. |
| 2015/0216237 A1 | 8/2015 | Wensley et al. |

FOREIGN PATENT DOCUMENTS

| | | |
|---|---|---|
| WO | WO-2014/177860 A1 | 11/2014 |
| WO | WO-2016/073709 A1 | 5/2016 |
| WO | WO-2016/096497 A1 | 6/2016 |
| WO | WO-2016/108694 A1 | 7/2016 |
| WO | WO-2016/124740 A1 | 8/2016 |

\* cited by examiner

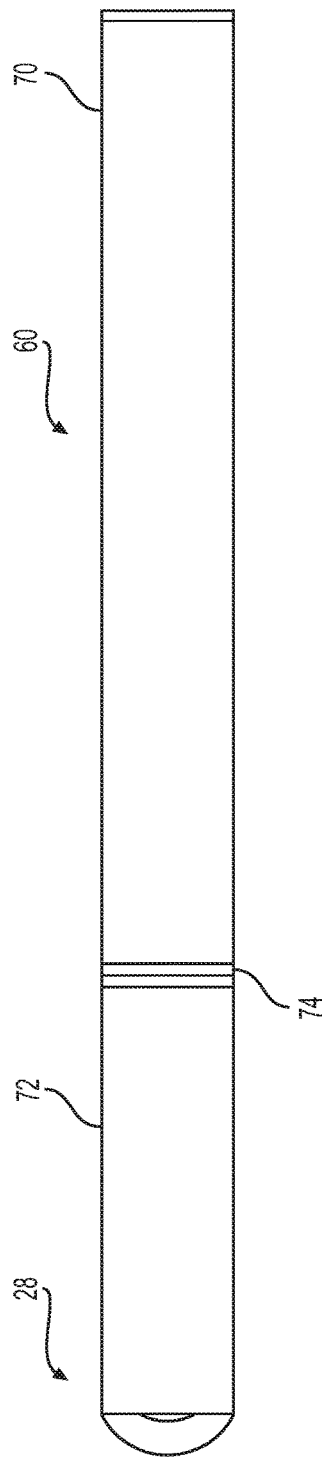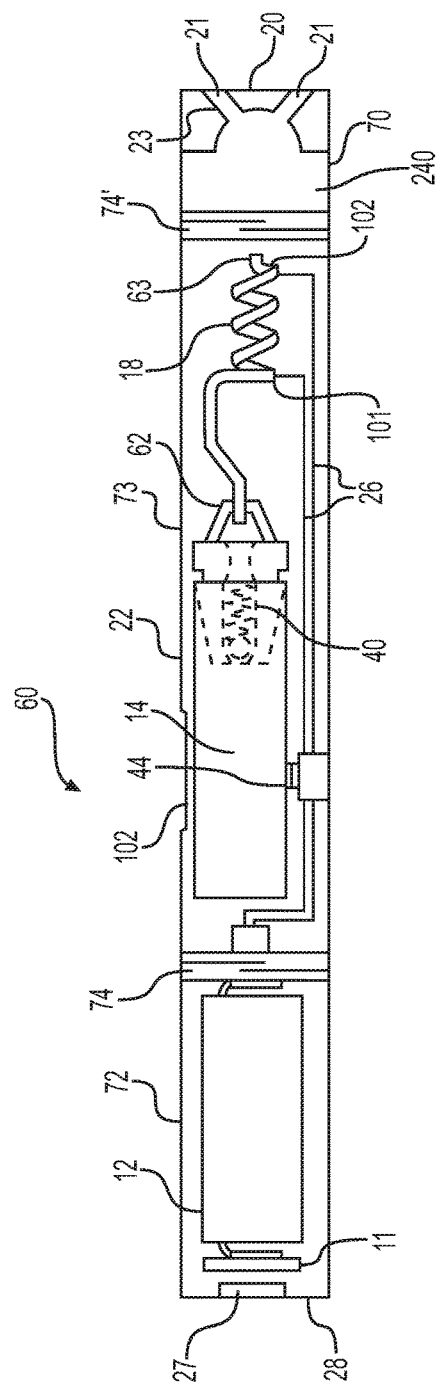

VENTURI EFFECT-DRIVEN FORMULATION DELIVERY IN E-VAPING DEVICES

BACKGROUND OF THE INVENTION

Field of the Invention

Example embodiments relate generally to a pre-vapor formulation delivery method and system and/or to a Venturi effect-based pre-vapor formulation delivery method and system.

Related Art

Electronic vaping devices are used to vaporize a liquid material into a vapor in order for an adult vaper to draw the vapor through one or more outlets of the device. These electronic vaping devices may be referred to as e-vaping devices. An e-vaping device may typically include several e-vaping elements such as a power supply section and a cartridge. The power supply section includes a battery, and the cartridge includes a heater along with a reservoir capable of holding the pre-vapor formulation or liquid material. The reservoir may include a winding of cotton or cellulose gauze or other fibrous material about an inner tube or about a portion of the reservoir. The cartridge typically includes the heater in communication with the pre-vapor formulation via a wick, the heater being configured to heat the pre-vapor formulation at the wick to produce a vapor. The pre-vapor formulation typically includes an amount of nicotine as well as a vapor former and possibly water, acids, flavorants and/or aromas. The pre-vapor formulation includes a material or combination of materials that may be transformed into a vapor. For example, the pre-vapor formulation may include a liquid, solid and/or gel formulation including, but not limited to, water, beads, solvents, active ingredients, ethanol, plant extracts, natural or artificial flavors, and/or vapor formers such as glycerine and/or propylene glycol.

The pre-vapor formulation included in the reservoir of the e-vaping device is driven to the mouth-end insert of the e-vaping device during operation thereof by an adult vaper. The manner in which the pre-vapor formulation is driven to the mouth-end insert has an effect on the rate of delivery as well as the amount of the pre-vapor formulation delivered to the adult vaper, which in turn affects the experience of the adult vaper.

SUMMARY OF THE INVENTION

At least one example embodiment relates to a Venturi effect-driven system of delivery of the pre-vapor formulation of an e-vaping device to a mouth-end insert thereof during operation of the e-vaping device.

In at least one example embodiment, an e-vaping device includes a mouth-end insert, a reservoir connectable to the mouth-end insert, the reservoir including an inner reservoir, a plurality of orifices distributed along a surface of the inner reservoir, and a power portion connectable to the reservoir. In some example embodiments, the inner reservoir is a concentric inner reservoir. In some example embodiments, the plurality of orifices are substantially homogeneously distributed along the surface of the inner reservoir.

In at least one example embodiment, the plurality of orifices are spaced at about 1.5 to about 2 times an average diameter of the plurality of orifices. For example, an average diameter of the plurality of orifices is between about 0.3 mm and about 0.8 mm, and an average thickness of a wall of the inner reservoir is between about 0.1 mm and about 0.4 mm.

In some example embodiments, the inner reservoir defines a narrow passageway and at least one wider passageway in a direction substantially parallel to a longitudinal direction of the e-vaping device. For example, the inner reservoir defines a narrow passageway between two wider passageways in a direction substantially parallel to a longitudinal direction of the e-vaping device. In some example embodiments, the narrow passageway has a width of about 0.5 mm to about 1.0 mm, and an average diameter of the plurality of orifices is between about 0.3 mm and about 0.8 mm.

In some example embodiments, the inner reservoir may have a substantially circular cross-section, a substantially rectangular cross-section, a substantially oval cross-section, or a substantially triangular cross-section.

In some example embodiments, the mouth-end insert includes a heater, and a portion configured to direct an amount of pre-vapor formulation onto the heater. The portion may be concentric and extend along a longitudinal direction of the e-vaping device. An angle between a surface of the reservoir, or an axis of the longitudinal direction of the e-vaping device, and the portion may be between about 30° and about 120°, and for example may be about 90°.

In at least one example embodiment, the e-vaping device delivers an amount of pre-vapor formulation that is correlated to the length of time the adult vaper draws on the mouth-end insert. For example, the longer the adult vaper draws on the mouth-end insert, the larger the amount of pre-vapor formulation is transferred from the reservoir and vaporized.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 1 is a side view of an e-vaping device;

FIGS. 2-4 are longitudinal cross-sectional views of an e-vaping device;

DETAILED DESCRIPTION

Figure 3:
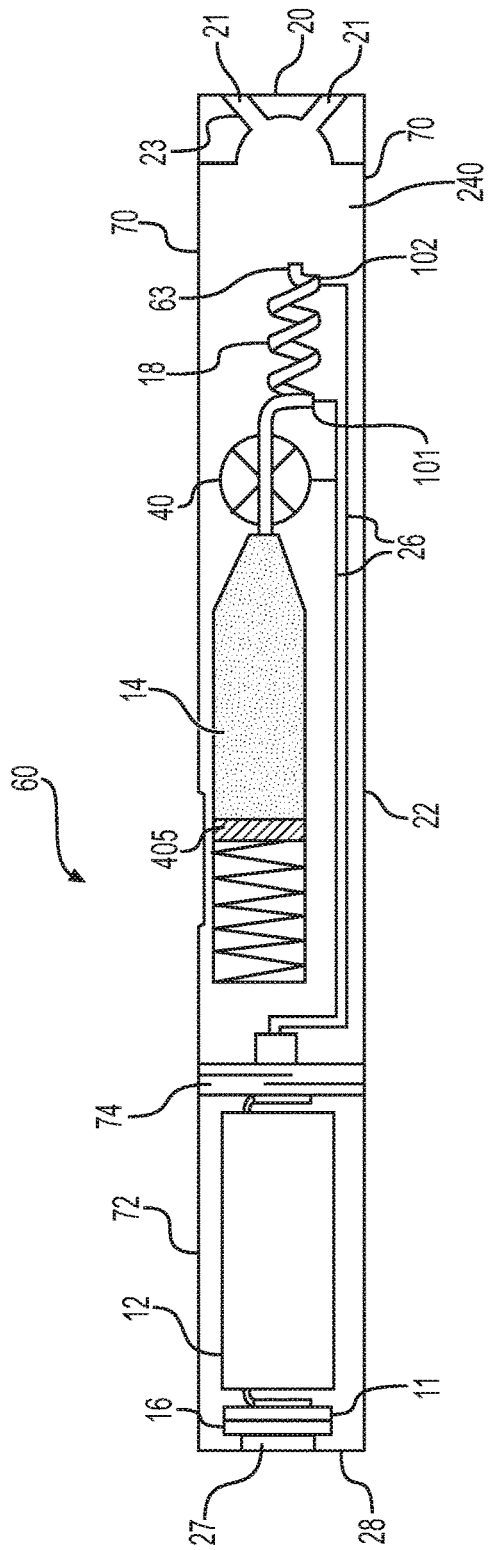

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations and/or elements, but do not preclude the presence or addition of one or more other features, integers, steps, operations, elements and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

As used herein, the term "vapor former" describes any suitable known compound or mixture of compounds that, in use, facilitates formation of a vapor and that is substantially resistant to thermal degradation at the operating temperature of the vapor-generating device. Suitable vapor-formers consist of various compositions of polyhydric alcohols such as propylene glycol. In at least one embodiment, the vapor former is propylene glycol.

FIG. 1 is a side view of an e-vaping device or a "cigalike" device 60, according to an example embodiment. In FIG. 1, the e-vaping device 60 includes a first section or cartridge 70 and a second section 72, which are coupled together at a threaded joint 74 or by other connecting structure such as a snug-fit, snap-fit, detent, clamp and/or clasp or the like. In at least one example embodiment, the first section or cartridge 70 may be a replaceable cartridge, and the second section 72 may be a reusable section. Alternatively, the first section or cartridge 70 and the second section 72 may be integrally formed in one piece. In at least one embodiment, the second section 72 includes a LED at a distal end 28 thereof.

FIG. 2 is a cross-sectional view of an example embodiment of an e-vaping device. As shown in FIG. 2, the first section or cartridge 70 can house a mouth-end insert 20, a capillary capillary tube 18, and a reservoir 14.

In some example embodiments, the reservoir 14 may be a wrapping of gauze about an inner tube (not shown). The reservoir 14 may include an outer wrapping of gauze surrounding an inner wrapping of gauze of the same or different material. In at least one example embodiment, the reservoir 14 may be constructed from an alumina ceramic in the form of loose particles, loose fibers, or woven or nonwoven fibers, or alternatively the reservoir 14 may be constructed from a cellulosic material such as cotton or gauze material or polymer material, such as polyethylene terephthalate in the form of a bundle of loose fibers. A more detailed description of the reservoir 14 is provided below.

The second section 72 can house a power supply 12, a control circuitry 11 configured to control the power supply 12, and a puff sensor 16. The puff sensor is configured to sense when an adult vaper is puffing on the e-vaping device 60, which triggers operation of the power supply 12 via the control circuitry 11 to heat the pre-vapor formulation housed in the reservoir 14 and form a vapor. A threaded portion 74 of the second section 72 can be connected to a battery charger, when not connected to the first section or cartridge 70, to charge the battery or power supply section 12.

In some example embodiments, the capillary tube 18 is formed of or includes a conductive material, and thus acts as its own heater by passing current through the tube. The capillary tube 18 may be any electrically conductive material capable of being resistively heated, while retaining the necessary structural integrity at the operating temperatures experienced by the capillary tube 18, and which is non-reactive with the pre-vapor formulation. Suitable materials for forming the capillary tube 18 are one or more of stainless steel, copper, copper alloys, porous ceramic materials coated with film resistive material, nickel-chromium alloys, and combinations thereof. For example, the capillary tube 18 is a stainless steel capillary tube 18 and serves as a heater via electrical leads 26 attached thereto for passage of direct or alternating current along a length of the capillary tube 18. Thus, the stainless steel capillary tube 18 is heated by resistance heating. Alternatively, the capillary tube 18 may be a non-metallic tube such as, for example, a glass tube. In such an embodiment, the capillary tube 18 is formed of or includes a conductive material capable of being resistively heated, such as, for example, stainless steel, nichrome or platinum wire, arranged along the glass tube. When the heater arranged along the glass tube is heated, pre-vapor formulation in the capillary tube 18 is heated to a temperature sufficient to at least partially volatilize pre-vapor formulation in the capillary tube 18.

In at least one embodiment, at least two electrical leads 26 are bonded to the metallic capillary tube 18. In at least one embodiment, one electrical lead 26 is coupled to a first, upstream portion 101 of the capillary tube 18 and a second electrical lead 26 is coupled to a downstream, end portion 102 of the capillary tube 18.

In operation, when an adult vaper puffs on the e-vaping device, the puff sensor 16 detects a pressure gradient caused by the puffing of the adult vaper, and the control circuitry 11 heats the pre-vapor formulation located in the reservoir 14 by providing power the capillary tube 18. Once the capillary tube 18 is heated, the pre-vapor formulation contained within a heated portion of the capillary tube 18 is volatilized and emitted out of the outlet 63, where the pre-vapor formulation expands and mixes with air and forms a vapor in mixing chamber 240.

As shown in FIG. 2, the reservoir 14 includes a valve 40 configured to maintain the pre-vapor formulation within the reservoir 14 and to open when the reservoir 14 is squeezed and pressure is applied thereto, which results in the reservoir 14 forcing the pre-vapor formulation through the outlet 62 of the reservoir 14 to the capillary tube 18. In at least one embodiment, the valve 40 opens when a critical, minimum pressure is reached so as to avoid inadvertent dispensing pre-vapor formulation from the reservoir 14. In at least one embodiment, the pressure required to press the pressure switch 44 is high enough such that accidental heating is avoided.

The power supply 12 of example embodiments can include a battery arranged in the second section 72 of the e-vaping device 60. The power supply 12 is configured to apply a voltage to volatilize the pre-vapor formulation housed in the reservoir 14.

In at least one embodiment, the electrical contacts or connection between the capillary tube 18 and the electrical leads 26 are substantially conductive and temperature resistant while the capillary tube 18 is substantially resistive so that heat generation occurs primarily along the capillary tube 18 and not at the contacts.

The power supply section or battery 12 may be rechargeable and include circuitry allowing the battery to be chargeable by an external charging device. In this case, the circuitry, when charged, provides power for a pre-determined number of puffs, after which the circuitry may have to be re-connected to an external charging device.

In at least one embodiment, the e-vaping device 60 may include control circuitry which can be on a printed circuit board 11. The control circuitry 11 may also include a heater activation light 27 that is configured to glow when the device is activated. In at least one embodiment, the heater activation light 27 comprises at least one LED and is at a distal end 28 of the e-vaping device 60 so that the heater activation light 27 illuminates a cap which takes on the appearance of a burning coal during a puff. Moreover, the heater activation light 27 can be configured to be visible to the adult vaper. The light 27 may also be configured such that the adult vaper can activate and/or deactivate the light 27 when desired, such that the light 27 would not activate during vaping if desired.

In at least one embodiment, the e-vaping device 60 further includes a mouth-end insert 20 having at least two off-axis, diverging outlets 21. In at least one embodiment, the mouth-end insert 20 includes at least two diverging outlets 21 (e.g., 3 to 8 outlets or more). In at least one embodiment, the outlets 21 of the mouth-end insert 20 are located at ends of off-axis passages 23 and are angled outwardly in relation to the longitudinal direction of the e-vaping device 60 (i.e., divergently). As used herein, the term "off-axis" denotes an angle to the longitudinal direction of the e-vaping device. Also, the mouth-end insert (or flow guide) 20 may include outlets uniformly distributed around the mouth-end insert 20 so as to substantially uniformly distribute vapor in an adult vaper's mouth during use.

In at least one embodiment, the e-vaping device 60 is about the same size as a tobacco-based product. In some embodiments, the e-vaping device 60 may be about 80 mm to about 110 mm long, for example about 80 mm to about 100 mm long and about 7 mm to about 10 mm in diameter.

The outer cylindrical housing 22 of the e-vaping device 60 may be formed of or include any suitable material or combination of materials. In at least one embodiment, the outer cylindrical housing 22 is formed at least partially of metal and is part of the electrical circuit connecting the control circuitry 11, the power supply 12 and the puff sensor 16.

As shown in FIG. 2, the e-vaping device 60 can also include a middle section (third section) 73, which can house the pre-vapor formulation reservoir 14 and the capillary tube 18. The middle section 73 can be configured to be fitted with a threaded joint 74' at an upstream end of the first section or cartridge 70 and a threaded joint 74 at a downstream end of the second section 72. In this example embodiment, the first section or cartridge 70 houses the mouth-end insert 20, while the second section 72 houses the power supply 12 and the control circuitry 11 that is configured to control the power supply 12.

FIG. 3 is a cross-sectional view of an e-vaping device according to an example embodiment. In at least one embodiment, the first section or cartridge 70 is replaceable so as to avoid the need for cleaning the capillary tube 18. In at least one embodiment, the first section or cartridge 70 and the second section 72 may be integrally formed without threaded connections to form a disposable e-vaping device.

As shown in FIG. 3, in other example embodiments, a valve 40 can be a two-way valve, and the reservoir 14 can be pressurized. For example, the reservoir 14 can be pressurized using a pressurization arrangement 405 configured to apply constant pressure to the reservoir 14. As such, emission of vapor formed via heating of the pre-vapor formulation housed in the reservoir 14 is facilitated. Once pressure upon the reservoir 14 is relieved, the valve 40 closes and the heated capillary tube 18 discharges any pre-vapor formulation remaining downstream of the valve 40.

Figure 4:
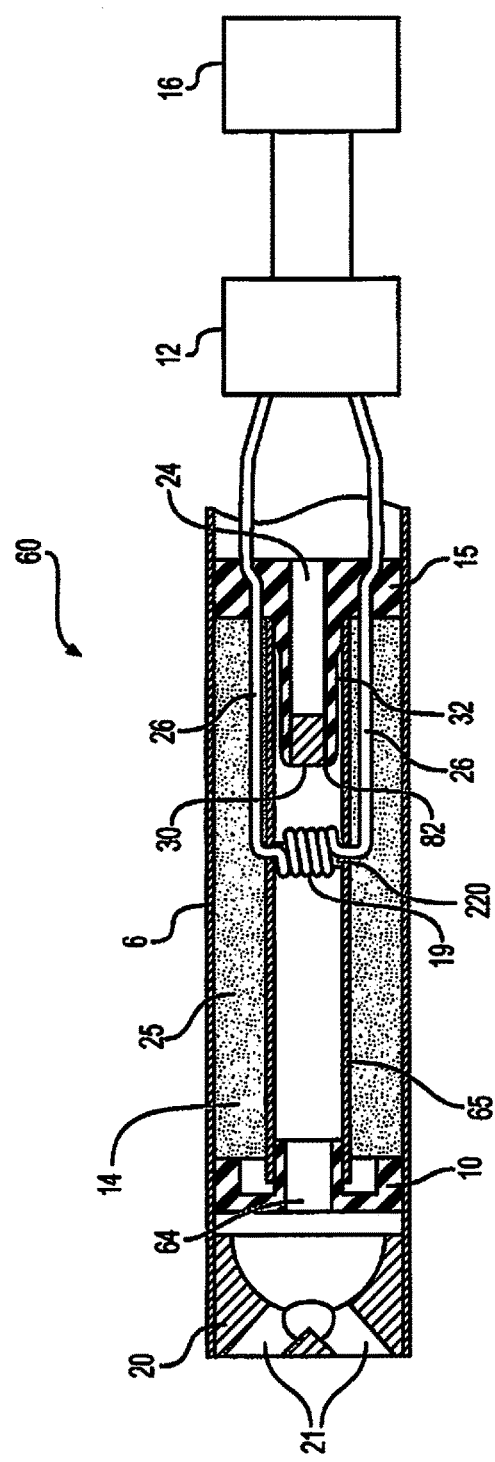

FIG. 4 is a longitudinal cross-sectional view of another example embodiment of an e-vaping device. In FIG. 4, the e-vaping device 60 can include a central air passage 24 in an upstream seal 15. The central air passage 24 opens to the inner tube 65. Moreover, the e-vaping device 60 includes a reservoir 14 configured to store the pre-vapor formulation. The reservoir 14 includes the pre-vapor formulation and optionally a storage medium 25 such as gauze configured to store the pre-vapor formulation therein. In an embodiment, the reservoir 14 is contained in an outer annulus between the outer tube 6 and the inner tube 65. The annulus is sealed at an upstream end by the seal 15 and by a stopper 10 at a downstream end so as to prevent leakage of the pre-vapor formulation from the reservoir 14. The heater 19 at least partially surrounds a central portion of the wick 220 such that when the heater is activated, the pre-vapor formulation in the central portion of the wick 220 is vaporized to form a vapor. The heater 19 is connected to the battery 12 by two spaced apart electrical leads 26. The e-vaping device 60 further includes a mouth end insert 20 having at least two outlets 21. The mouth end insert 20 is in fluid communication with the central air passage 24 via the interior of inner tube 65 and a central passage 64, which extends through the stopper 10.

The e-vaping device 60 may include an air flow diverter comprising an impervious plug 30 at a downstream end 82 of the central air passage 24 in seal 15. Preferably, the central air passage 24 is an axially extending central passage in seal 15, which seals the upstream end of the annulus between the outer and inner tubes 6, 65. The radial air channel 32 directing air from the central passage 20 outward toward the inner tube 65. In operation, when an adult vaper puffs on the e-vaping device, the puff sensor 16 detects a pressure gradient caused by the puffing of the adult vaper, and the control circuitry 11 heats the pre-vapor formulation located in the reservoir 14 by providing power the heater 19.

Figure 5:
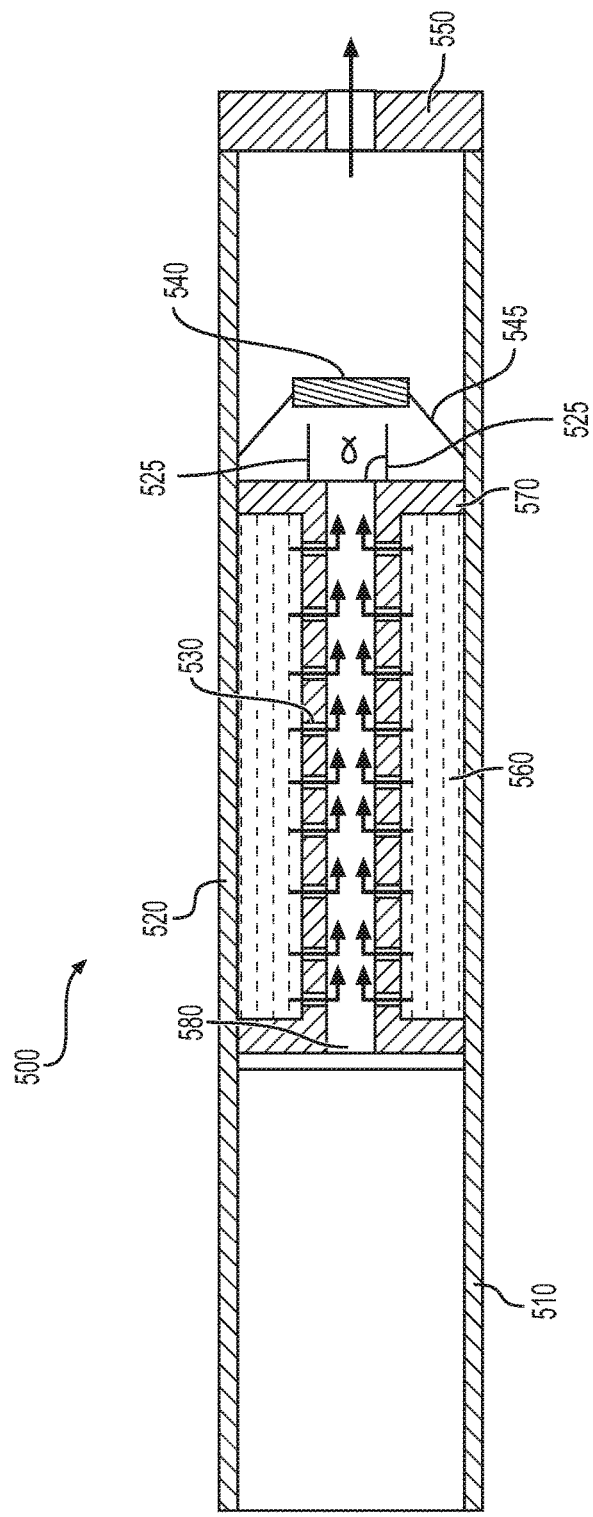
FIG. 5 is a longitudinal cross-sectional view of an e-vaping device, according to at least one example embodiment.

FIG. 5 is a longitudinal cross-sectional view of an e-vaping device, according to at least one example embodiment. In FIG. 5, the e-vaping device 500 includes a power portion 510 that includes a power source such as, for example, a battery (not shown), a vaporization portion 520 and a mouth-end insert 550. In the vaporization portion or reservoir 570, the pre-vapor formulation 560 is housed in a reservoir 570. In some example embodiments, the reservoir 570 may be concentrically configured so as to surround an axial passage 580, the axial passage 580 being between the battery portion 510 and a heating portion of the e-vaping device 500 that includes the heater 540 in a longitudinal direction or axis of the e-vaping device 500. An interior surface of the reservoir 570 that surrounds the axial passage 580 includes a plurality of orifices 530 along a substantial length of the passage 580 along the axis of the e-vaping device 500.

In operation, when a negative pressure is created during operation of the e-vaping device by an adult vaper, for example, when the adult vaper draws through the mouth-end insert 550, small portions of the pre-vapor formulation 560 such as, for example, small droplets, are drawn towards the mouth-end insert 550 by the negative pressure. In some example embodiments, because the diameter of the passage 580 is sufficiently small, the pressure created by the drawing action of the adult vaper via a Venturi effect is such that droplets of the pre-vapor formulation 560 are extracted from the reservoir 570 and through the orifices 530 and are transferred through the passage 580 to the mouth-end insert 550. A heater 540, located between the reservoir 570 and the mouth-end insert 550, heats up the droplets and generates a vapor that is emitted out of the e-vaping device 500 via the mouth-end insert 550.

In some example embodiments, the orifices 530 may be densely distributed at the interior surface of the reservoir 570. For example, the orifices 530 may be spaced at about 1.5 to about 2 times the average diameter of the orifices 530. The average diameter of the orifices 530 is typically dependent on the viscosity of the pre-vapor formulation 560, and may be in the range of, for example, about 0.3 mm to about 0.8 mm, and for example 0.35 mm, 0.40 mm, 0.45 mm, 0.50 mm, 0.55 mm, 0.60 mm, 0.65 mm, 0.70 mm and 0.75 mm. Typically, the more viscous the pre-vapor formulation, the larger the orifice should be. For example, in cases where a first portion of the reservoir 570 houses a liquid having one viscosity, and a second portion of the reservoir 570 houses a liquid having a different viscosity, then the orifices 530 in the first and second portions of the reservoir 570 may have different sizes to account for the differences in viscosity between the liquids in both portions of the reservoir 570.

In some example embodiments, the wall thickness at the interior surface of the reservoir 570, adjacent to the passage 580, is between about 0.1 mm and about 0.4 mm. Typically, a thin reservoir wall provides better transfer of pre-vapor formulation 560 to the air passage 580 because of the shorter travel distance of the pre-vapor formulation 560 when transferring from inside the reservoir 570 to outside the reservoir 570 through the orifices 530.

In some example embodiments, the heater 540 may be connected to the battery (not shown) included in the power section 510 via the leads 545. The heater may be, for example, a coil heater, a flat heater or a mesh heater.

According to various example embodiments, a directing or funneling portion 525 may be provided between the reservoir 570 and the heater 540, the directing portion 525 being configured to direct the pre-vapor formulation onto the heater 540. For example, the directing portion 525 may be a funnel-like portion. In some example embodiments, the directing portion 525 may be concentric and may extend in the longitudinal direction of the e-vaping device 500. Although the portion 525 is illustrated in FIG. 5 as being substantially perpendicular to the surface of the reservoir 570, the portion 525 may be angled with respect to the surface of the reservoir 570. For example, the angle α between the surface of the reservoir 570 and the portion 525 may be between about 30° and 120°. In FIG. 5, the angle α is illustrated to be about 90°.

Figure 6A:
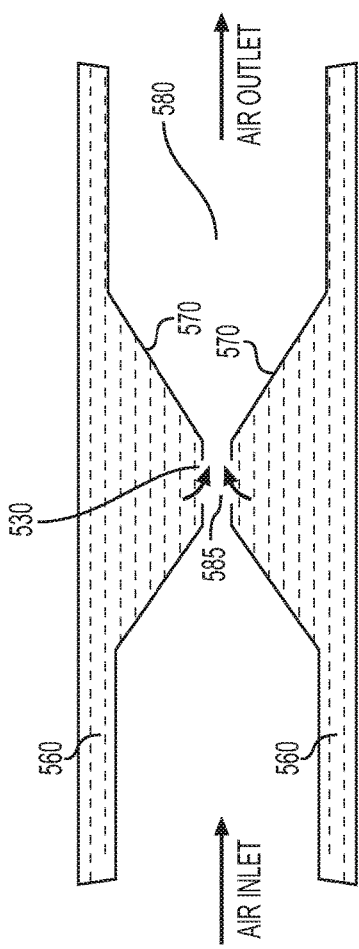
FIGS. 6(*a*)-(*b*) illustrate a cross-section of a Venturi effect-based reservoir for a pre-vapor formulation, according to at least one example embodiment.
Figure 6B:
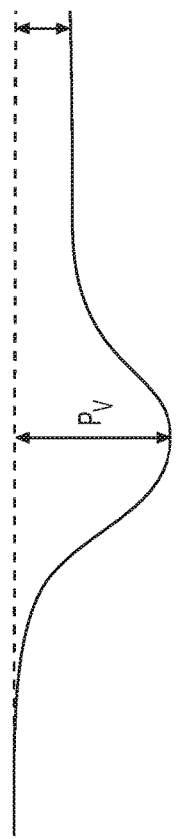

FIGS. 6(a)-(b) illustrate a cross-section of a Venturi effect-based reservoir for a pre-vapor formulation, and the resulting air pressure profile, according to at least one example embodiment. In FIG. 6(a), the reservoir 570 defines a narrower passage 585 at a portion of the passage 580, the narrower passage 585 being sufficiently narrow to, due to a Venturi effect, provide a large enough negative pressure, during operation of the e-vaping device by an adult vaper, to transfer a sufficient amount of pre-vapor formulation 560 from the reservoir 570 to the mouth-end insert (not shown) via the orifices 530. The reservoir 570 may have a tapered, or funnel-like, inside surface extending from the narrowest passage 585 to the widest passage 580 on each side of the narrow passage 585 in a longitudinal direction of the e-vaping device. Due to the narrow width of the passage 585, which creates a higher negative pressure at that location due to the Venturi effect, droplets of pre-vapor formulation are more efficiently transferred outside of the reservoir 570 towards the mouth-end insert (not shown) in a longitudinal direction of the e-vaping device. The extracted droplets are then heated and vaporized before being received by the adult e-vaper during operation of the e-vaping device.

FIG. 6(b) illustrates a pressure profile along the passage 580. Specifically, FIG. 6(b) shows that the largest negative pressure occurs at the narrowest passage 585 due to the Venturi effect. Away from the narrowest passage 585, the pressure increases in correlation with the widening of the passageway 580 but remains negative due to the continuing use of the e-vaping device by an adult vaper. Because the pressure along the passages 585 and 580 is reliably negative, droplets of pre-vapor formulation 560 are transported from the reservoir 570 to the mouth-end insert (not shown) via the passages 585 and 580.

Figure 7:
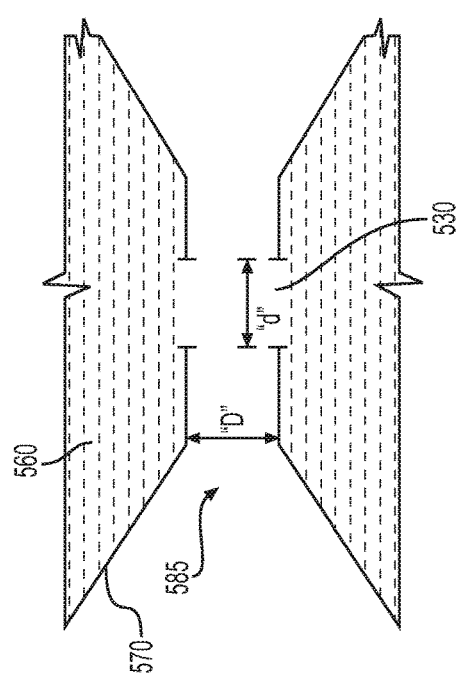
FIG. 7 is a detailed cross-section of the Venturi effect-based reservoir for a pre-vapor formulation, according to at least one example embodiment.

FIG. 7 is a detailed cross-section of a Venturi effect-based reservoir for a pre-vapor formulation, according to at least one example embodiment. In FIG. 7, the reservoir 570, including the pre-vapor formulation 560, includes a narrow passage 585 along a longitudinal axis of the e-vaping device. An inner surface of the reservoir 570 includes at least one orifice 530, and the passage 585 has an average diameter "D." In some example embodiments, the diameter "D" of the passage 585 may be in the range of about 0.5 mm to about 1.0 mm. In some example embodiments, the diameter "d" of the orifice 530 may be in the range of about 0.3 mm to about 0.8 mm.

Figure 8B:
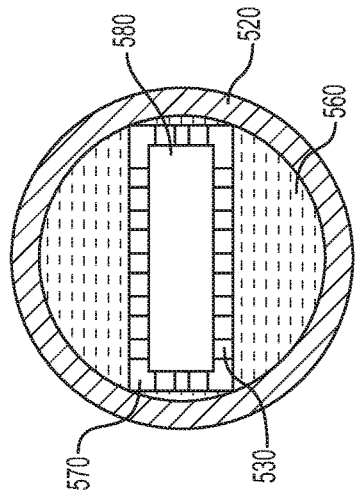
FIGS. 8(*a*)-(*d*) are cross-sections of a pre-vapor formulation reservoir, according to example embodiments.
Figure 8D:
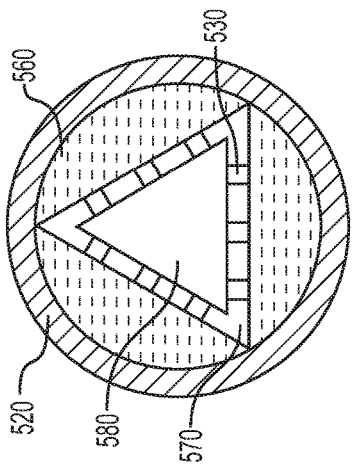
Figure 8A:
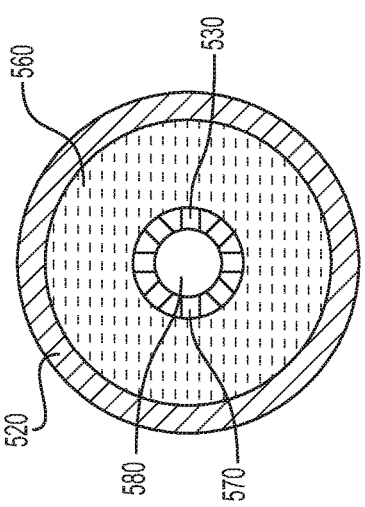
Figure 8C:
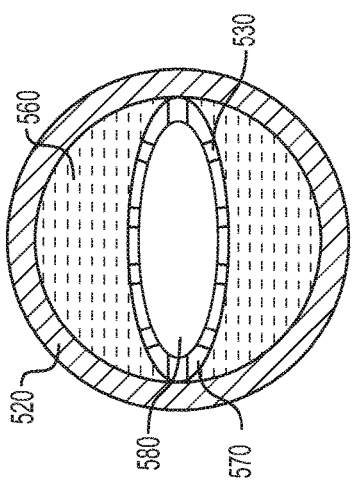

FIGS. 8(a)-(d) illustrate cross-sections of a pre-vapor formulation reservoir, according to example embodiments. FIGS. 8(a)-(d) illustrate a reservoir 570 having different cross-sectional shapes. For example, FIG. 8(a) illustrates a reservoir 570 with an interior surface having a substantially circular cross-section around the longitudinal axis of the e-vaping device. The reservoir 570 includes the pre-vapor formulation 560 and, at an interior surface thereof, a plurality of orifices 530. In FIG. 8(b), the cross-section of the reservoir 570 is substantially rectangular. FIG. 8(c) illustrates a substantially oval cross-section, and FIG. 8(d) illustrates a substantially triangular cross-section. Although specific cross-sections are illustrated in FIGS. 8(a)-(d), the reservoir 570 according to example embodiments may include other cross-sectional shapes.

Example embodiments having thus been described, it will be obvious that the same may be varied in many ways. Such variations are not to be regarded as a departure from the intended spirit and scope of example embodiments, and all modifications as would be obvious to one skilled in the art are intended to be included within the scope of the following claims.

What is claimed is:

1. An e-vaping device, comprising:
    a mouth-end insert;
    a reservoir connected to the mouth-end insert;
    the reservoir having a plurality of orifices distributed along an interior surface thereof, at least one of the plurality of orifices being in direct fluid communication with a liquid pre-vapor formulation;
    a power portion connected to the reservoir;
    a heater on a longitudinal axis between the reservoir and the mouth-end insert, the heater being separate from the reservoir in a longitudinal direction of the e-vaping device; and
    a directing portion between the reservoir and the heater configured to direct an amount of the liquid pre-vapor formulation to the heater.

2. The e-vaping device of claim 1, wherein the reservoir is a concentric reservoir.

3. The e-vaping device of claim 1, wherein the plurality of orifices are substantially homogeneously distributed along the interior surface of the reservoir.

4. The e-vaping device of claim 1, wherein the plurality of orifices are spaced at about 1.5 to about 2 times an average diameter of the plurality of orifices.

5. The e-vaping device of claim 1, wherein an average diameter of the plurality of orifices is between about 0.3 mm and about 0.8 mm.

6. The e-vaping device of claim 1, wherein an average thickness of a wall of the reservoir is between about 0.1 mm and about 0.4 mm.

7. The e-vaping device of claim 1, wherein the reservoir defines a narrow passageway and at least one wider passageway in the longitudinal direction of the e-vaping device.

8. The e-vaping device of claim 1, wherein the reservoir defines a narrow passageway between two wider passageways in the longitudinal direction of the e-vaping device.

9. The e-vaping device of claim 7, wherein the narrow passageway has a width of about 0.5 mm to about 1.0 mm.

10. The e-vaping device of claim 7, wherein an average diameter of the plurality of orifices is between about 0.3 mm and about 0.8 mm.

11. The e-vaping device of claim 1, wherein the reservoir has a substantially rectangular cross-section.

12. The e-vaping device of claim 1, wherein the reservoir has a substantially oval cross-section.

13. The e-vaping device of claim 1, wherein the reservoir has a substantially triangular cross-section.

14. The e-vaping device of claim 1, wherein the portion is substantially concentric.

15. The e-vaping device of claim 1, wherein the portion extends away from a surface of the reservoir in the longitudinal direction of the e-vaping device.

16. The e-vaping device of claim 15, wherein an angle between the surface of the reservoir and the portion is between about 30° and about 120°.

17. The e-vaping device of claim 16, wherein the angle between the surface of the reservoir and the portion is about 90°.

18. The e-vaping device of claim 1, wherein the reservoir has a substantially polygonal cross-section.

19. The e-vaping device of claim 1, wherein the reservoir has a substantially circular cross-section.

* * * * *